(12) United States Patent
Dalvi

(10) Patent No.: US 12,011,559 B2
(45) Date of Patent: Jun. 18, 2024

(54) MULTIPLE ENTRY, SINGLE LUMEN DILATOR WITH A DELIVERY SHEATH

(71) Applicants: Bharat V. Dalvi, Mumbai (IN); Ziyad M. Hijazi, San Diego, CA (US)

(72) Inventor: Bharat V. Dalvi, Mumbai (IN)

(73) Assignees: Bharat V. Dalvi, Maharashtra (IN); Zihad M. Hijazi, San Diego, CA (US)

( * ) Notice: Subject to any disclaimer, the term of this patent is extended or adjusted under 35 U.S.C. 154(b) by 789 days.

(21) Appl. No.: 16/972,653

(22) PCT Filed: Jun. 6, 2019

(86) PCT No.: PCT/IB2019/054714
§ 371 (c)(1),
(2) Date: Dec. 7, 2020

(87) PCT Pub. No.: WO2019/234675
PCT Pub. Date: Dec. 12, 2019

(65) Prior Publication Data
US 2021/0085937 A1    Mar. 25, 2021

(30) Foreign Application Priority Data

Jun. 7, 2018  (IN) .............................. 201821021403

(51) Int. Cl.
*A61M 29/00*      (2006.01)
*A61M 25/00*      (2006.01)
(Continued)

(52) U.S. Cl.
CPC .......... *A61M 29/00* (2013.01); *A61M 25/007* (2013.01); *A61M 25/0662* (2013.01);
(Continued)

(58) Field of Classification Search
CPC .... A61M 2025/018; A61M 2025/0681; A61M 25/007; A61M 25/01; A61M 25/0662;
(Continued)

(56) References Cited

U.S. PATENT DOCUMENTS

| 4,769,005 A |   | 9/1988 | Ginsburg et al. |
|---|---|---|---|
| 4,932,413 A | * | 6/1990 | Shockey ........... A61M 25/0172 604/510 |

(Continued)

FOREIGN PATENT DOCUMENTS

| EP | 2233168 A1 | 9/2010 |
|---|---|---|
| EP | 2444115 A1 | 4/2012 |

OTHER PUBLICATIONS

International Search Report dated Oct. 28, 2019, Application No. PCT/IB2019/054714.

(Continued)

*Primary Examiner* — Mohamed G Gabr
(74) *Attorney, Agent, or Firm* — The Dobrusin Law Firm, P.C.; Eric R. Kurtycz

(57) ABSTRACT

A single lumen, multiple entry dilator sheath assembly is provided for delivering medical devices in different parts of cardiovascular system. The multiple holes allow multiple guidewires to enter the dilator-delivery sheath system distally and exit from a single lumen proximally thereby providing extra support to the delivery system while tracking over complex paths. Such a multi guide wire system has a definite advantage even over a two-wire system because, although two wire system may offer better support as compared to single wire, it will not be as good as a four wire system. Also, in two wire system the wires are fixed in their position and therefore overcoming the memory of sheath and dilator system will not be as good as with multi-wire (Continued)

Sheath and Dilator assembly with dilator having multiple holes of entry system because of the ability to use the multiple entry holes in various permutations and combinations.

8 Claims, 4 Drawing Sheets

(51) Int. Cl.
*A61M 25/06* (2006.01)
*A61M 25/09* (2006.01)

(52) U.S. Cl.
CPC ..... *A61M 25/09* (2013.01); *A61M 2025/0681* (2013.01); *A61M 2210/12* (2013.01); *A61M 2210/125* (2013.01)

(58) Field of Classification Search
CPC .. A61M 25/09; A61M 29/00; A61M 2210/12; A61M 2210/125
See application file for complete search history.

(56) References Cited

U.S. PATENT DOCUMENTS

| | | | |
|---|---|---|---|
| 5,342,295 A | 8/1994 | Imran | |
| 6,746,411 B2 | 6/2004 | Khaw | |
| 2012/0296275 A1* | 11/2012 | Martin | A61M 25/0662 604/103.05 |
| 2013/0304030 A1 | 11/2013 | Gray et al. | |
| 2014/0121641 A1 | 5/2014 | Fischell et al. | |

OTHER PUBLICATIONS

Written Opinion dated Oct. 28, 2019, Application No. PCT/IB2019/054714.

* cited by examiner

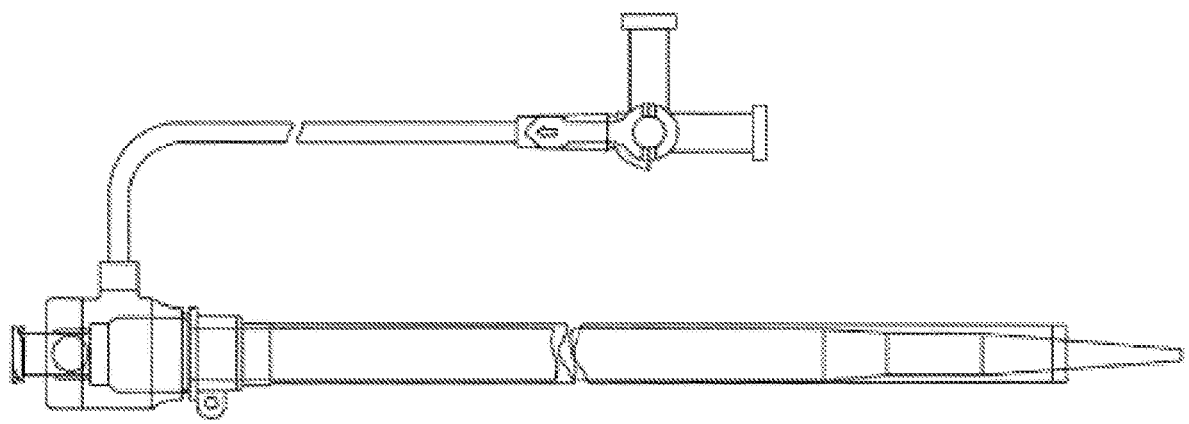
Figure 1: (Prior Art) Showing Sheath and Dilator assembly with dilator having single hole entry
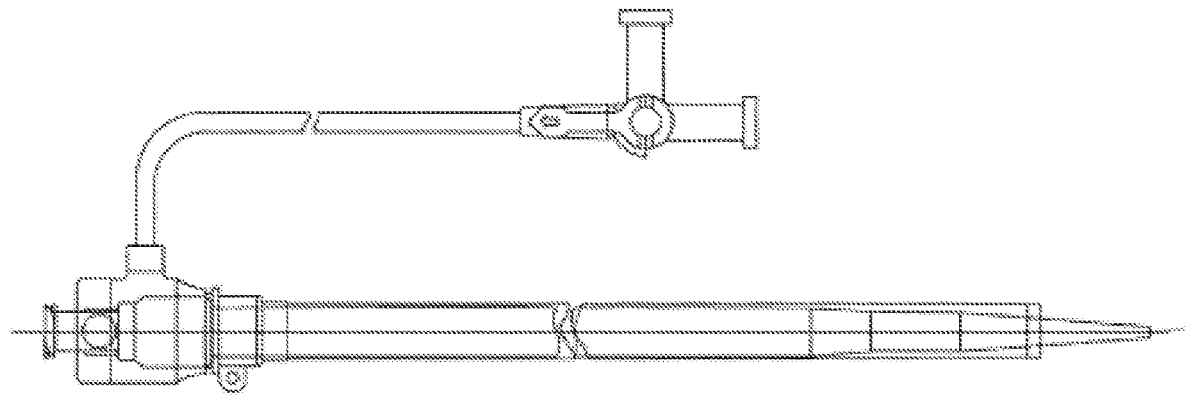
Figure 2: (Prior Art) Sheath and Dilator assembly having single hole entry with guide-wire passing through it

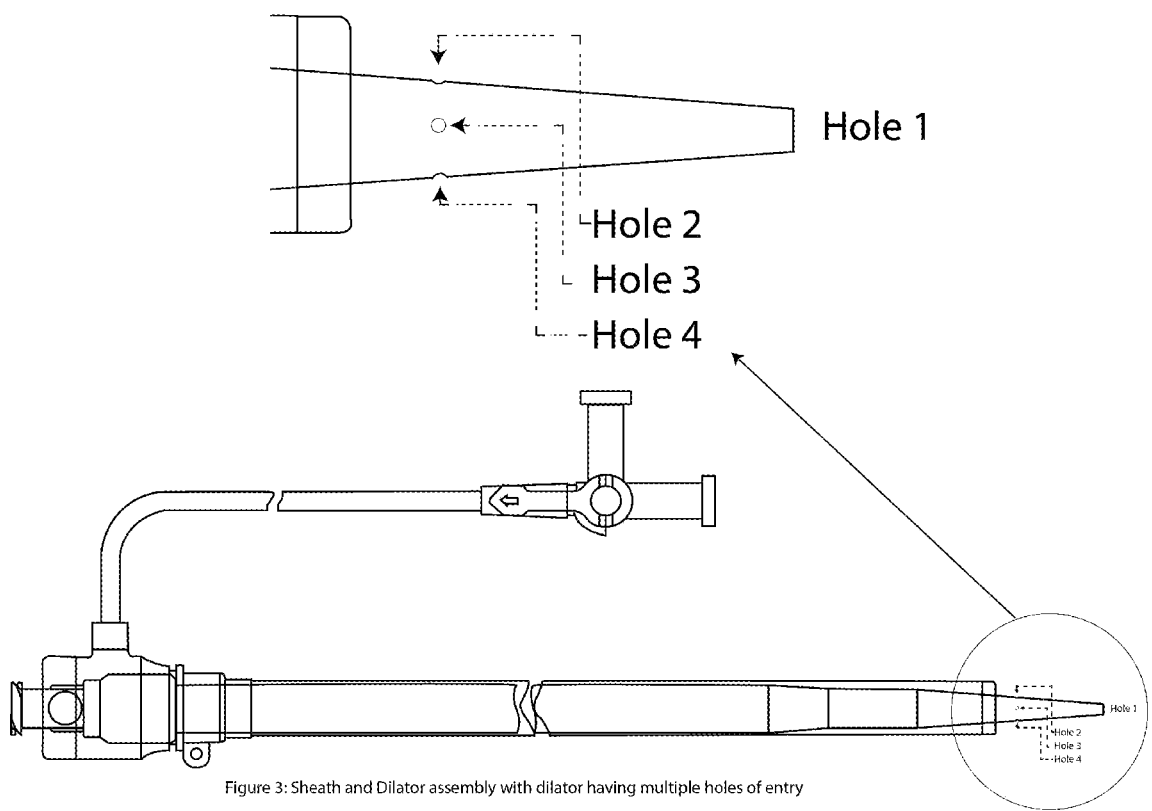
Figure 3: Sheath and Dilator assembly with dilator having multiple holes of entry

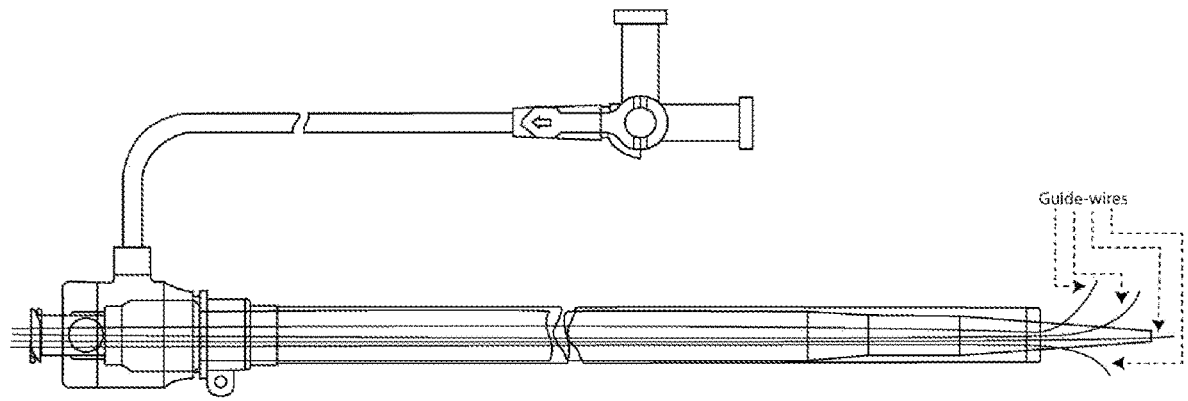
Figure 4: Sheath and Dilator assembly with dilator having a single port with multiple holes of entry with guide-wires passing through them
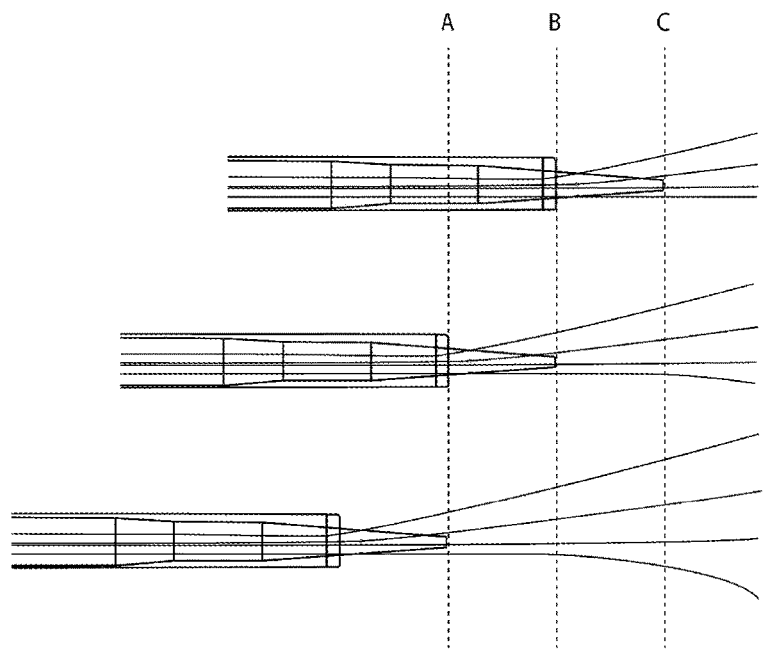
Figure 5: Sheath and Dilator assembly tracked over multiple guide-wires from point A to B to C

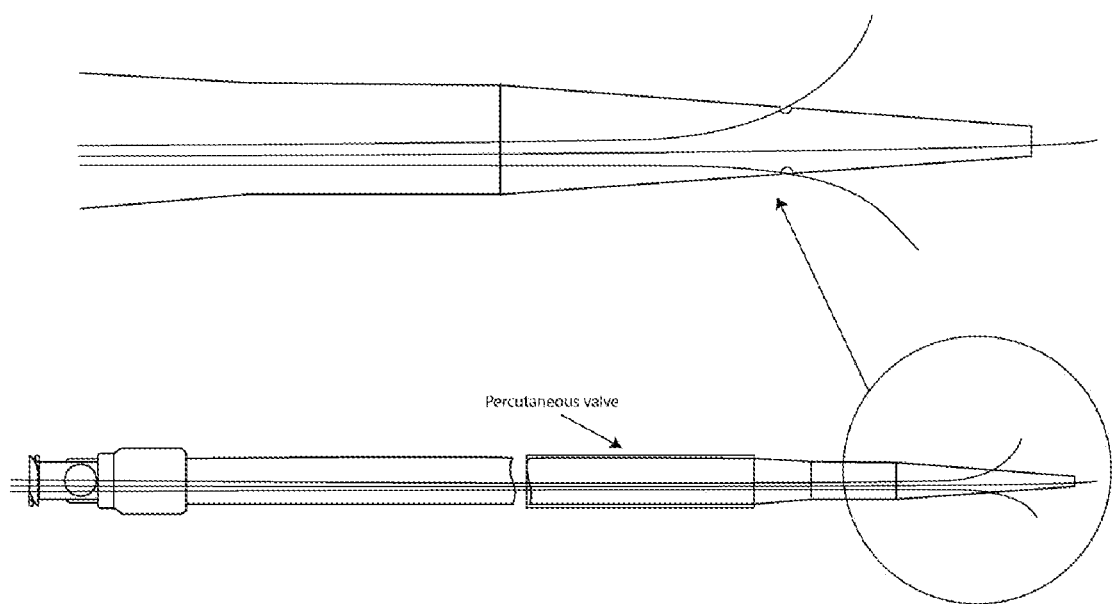
Figure 6: Percutaneous valve mounted over delivery system with multiple holes for multiple guide-wires

MULTIPLE ENTRY, SINGLE LUMEN DILATOR WITH A DELIVERY SHEATH

FIELD OF INVENTION

The present invention relates generally to a dilator-sheath assembly, and more particularly, to a multiple entry, single lumen dilator with a delivery sheath for tracking it over complex paths/passages. The same can be also used for percutaneous valve delivery system as well as for percutaneously delivering perforated vascular grafts (covered stents) in the vessels with side branches to avoid side branch occlusion

BACKGROUND ART

Delivery sheaths are used for delivering stents or percutaneous valves in different parts of cardiovascular system and are made of different sizes from 4 Fr to 22 Fr. These sheaths comprise a hollow tube with a hemostatic valve and a dilator. The purpose of the dilator is to go through skin and subcutaneous tissue at the point of entry into a vessel or any other organ such as but not limited to heart and liver.

Typically, the delivery sheath-dilator assembly is made to track over a single guide wire to reach a desired destination site. For this purpose, there is a single hole at the tip of prior art dilator as shown in FIG. 1, through which the prior art delivery system is threaded over a single guide wire as shown in FIG. 2 and then slowly pushed forward to the intended destination. As the sheath gets larger in size, the ability to track a complex course especially in the main pulmonary artery or its branches becomes more difficult. This point of destination is particularly difficult to reach because it involves two circuitous bends, one at the level of the right ventricular inflow and the other at the right ventricular outflow. One of the ways to overcome this problem is to use a very stiff guide wire which helps in tracking these bends. In some cases, however, even very stiff wire is unsuccessful in pushing the dilator-sheath assembly forward to its desired destination. This is due to the fact that single guide wire, no matter how stiff, is unable to support the large sheath dilator system.

For these reasons, it is desirable to have a delivery sheath-dilator system that can track over complex paths and sharp bends in addition to overcoming its memory of following one particular path which if inappropriate can frustrate the efforts of getting the system to its desired position.

Reference is made to U.S. Pat. No. 4,769,005A which discloses a guiding sheath having plurality of axial lumens that project laterally from the body at preselected angles so that, when inserted there through, the guidewire or catheter will exit at said preselected angle to facilitate directing the guidewire or catheter to the proper location within the vascular system. The invention allows selective positioning of the guidewire or catheter within the vascular system. The guiding sheath is positioned first and then the guidewires are introduced through the lumens to a predetermined position.

Reference is made to U.S. Pat. No. 5,342,295 which discloses a multi-lumen introducer adapted to be inserted into a vessel of the patient, wherein the introducer can receive a plurality of catheters through its multiple ports. The invention facilitates placing of multiple catheters through multiple lumens of the delivery catheter.

Reference is also made to U.S. Pat. No. 6,746,411B2 disclosing multiple exitable lumen guidewire sheath for the treatment of multiple branch vascular lesions. The single or multiple exitable lumens are used for the guidance of medical devices used in interventional medicine. The reference focuses on separating the guidewires prior to deployment and dilation of balloon and stent or other selected intra-vascular medical device.

Reference is further made to US20130304030A1 which discloses a medical guidewire system with plurality of parallel guidewires including a jacket, at least two guide wires and a handle. The purpose of the invention is to get one or more guidewires at a place so as to provide a trackable yet flexible path.

Yet another reference is made to US20140121641A1 disclosing an intravascular catheter for peri-vascular and/or peri-urethral tissue ablation that includes multiple needles advanced through guide tubes for injecting an ablative fluid. The reference discloses an assembly for providing radial ("backup") support for the needle guiding elements that provide resistance to the guiding elements backing away from the interior surface as the needles are advanced into the wall of the vessel.

The prior art solutions discussed in the references above relate to overcoming limitations of single port delivery systems by utilizing multiple guidewires or catheters. However, in contrast to the references, the present invention provides unique design of dilator sheath assembly and comprises of a sheath having single lumen and a dilator with a single port of exit but with multiple holes of entry. Moreover, unlike the cited references, where the guiding sheath is positioned first and subsequently guidewires/catheters are introduced through various lumens, the present invention allows multiple guide wires to be placed in an artery/arteries or a vein/veins or a heart chamber first and then the dilator-delivery sheath or a percutaneous valve assembly or covered vascular graft assembly can be introduced over these multiple guidewires to the desired destination. By doing so, extra support is provided to the delivery system while tracking to a point of interest in a complex path. Also, variable orientation of the multiple guide wires may help in overcoming the memory of the system which is characteristic of a single guide wire use.

SUMMARY

The following presents a simplified summary of the invention to provide basic understanding of some aspects of the invention, neither to identify the critical elements nor to delineate the scope of the invention. Its sole purpose is to present some concept of the invention in a simplified form, as a prelude to a more detailed description of the invention presented later.

An object of the present invention is to provide a multiple entry, single lumen dilator with delivery sheath for tracking over complex circuitous paths.

Accordingly, an aspect of the present invention relates to a single exit-multiple entry dilator with a delivery sheath comprising multiple holes located on the distal end of the dilator which has a single lumen all along its course including at the point of exit, large enough for accommodating multiple guidewires. The system can be used as usual, with single guidewire, or in case of difficulty tracking inside the heart, or vascular system, the same assembly can be used over multiple guidewires.

Another aspect of present invention relates to a sheath-dilator assembly for tracking inside the heart, or vascular system comprising a dilator with a single lumen at the proximal end and all along its length having multiple holes on distal end to accommodate more than one guide wires.

One of the holes is located at the tip of the dilator while the others are located proximally to the distal tip of the dilator but distal to the distal tip of the sheath. The assembly further discloses the number of guide wires and corresponding holes to be more than one, preferably two to six, most preferably two to three.

Another aspect of present invention relates to a sheath-dilator assembly for tracking inside the heart, or vascular system comprising a dilator with a single lumen at the proximal end and all along its length having multiple holes on distal end to accommodate more than one guide wires. The assembly may further comprise sheath which is coupled to the dilator in such a way that guide wires enter the dilator-sheath assembly through the holes allocated for each guide wires, run through the single lumen of the dilator and exit from the proximal single hole of the sheath-dilator assembly.

Yet another aspect of present invention relates to a sheath-dilator assembly for tracking inside the heart, or vascular system comprising a dilator with a single lumen at the proximal end and all along its length having multiple holes on distal end to accommodate more than one guide wires. The assembly further comprises dilator which is straight or curved.

Yet another aspect of present invention relates to a sheath-dilator assembly discloses the number of guide wires and corresponding holes to be more than one, preferably two to six, most preferably two to three. The assembly further comprises dilator which is adapted to be straight or curved. The sheath is further selected from 12 Fr sheath, 14 Fr sheath, 16 Fr sheath, 18 Fr sheath, 20 Fr sheath, 22 Fr sheath, 24 Fr sheath and 26 Fr sheath.

Other aspects, advantages and salient features of the invention will become apparent to those skilled in the art from the detailed description, which, taken in conjunction with the annexed drawings, discloses exemplary embodiments of the invention.

BRIEF DESCRIPTION OF THE ACCOMPANYING DRAWINGS

The above and other features, aspects, and advantages of the subject matter will be better understood with regard to the following description and accompanying drawings.

FIG. 1 illustrates a sheath-dilator assembly with a single lumen dilator with a single entry hole existing in the prior art.

FIG. 2 illustrates a sheath-dilator assembly with a single lumen dilator with single guide wire entering from the hole located at the tip of the dilator of the prior art.

FIG. 3 illustrates a sheath-dilator assembly with a single lumen dilator having multiple holes at its distal end; one at the tip and the rest of them proximal to the tip of the dilator but distal to the distal end of the sheath.

FIG. 4 illustrates the proximal end of the single lumen dilator-sheath assembly with the dilator port being of adequate size to accommodate 4 guide wires of 0.035" diameter FIGS. 5 (a), (b) and (c) illustrate sheath-single lumen multiple entry dilator-sheath system tracking over multiple wires from the point A to B to C.

FIG. 6 shows a percutaneous valve mounted over a delivery system with multiple holes for passing multiple wires to give adequate support for the large and bulky system to track over.

Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION

The following description with reference to the accompanying drawings is provided to assist in a comprehensive understanding of exemplary embodiments of the invention. It includes various specific details to assist in that understanding but these are to be regarded as merely exemplary.

Accordingly, those of ordinary skill in the art will recognize that various changes and modifications of the embodiments described herein can be made without departing from the scope of the invention. In addition, descriptions of well-known structure and method are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

Features that are described and/or illustrated with respect to one embodiment may be used in the same way or in a similar way in one or more other embodiments and/or in combination with or instead of the features of the other embodiments.

It should be emphasized that the term "comprises/comprising" if used in this specification is taken to specify the presence of stated features, integers, steps or component but does not preclude the presence or addition of one or more other features, integers, steps, components or groups thereof.

In accordance with one embodiment of the present invention there is described a single lumen, multiple entry dilator with a delivery sheath comprising a dilator with a single lumen at the proximal end and all along its length having multiple holes on distal end. One hole is located at the tip of the dilator while the others are located proximally to the distal tip of the dilator but distal to the distal tip of the sheath. Each of these holes is capable of accommodating a single guide wire. As a result, this single lumen multiple entry dilator-guide wire system can be made to track over multiple guidewires simultaneously. This will facilitate multiple guidewires to support the dilator-sheath assembly while tracking over a complex path such as but not limited to main pulmonary artery or its branches and reach a desired destination. Further, as force is distributed in different directions due to different orientation of the guide wires, the present invention has the ability to overcome memory of the system which is unique to the single guide wire system.

According to the present invention, the dilator-sheath assembly comprises a dilator with multiple holes at distal end, wherein one hole is at the tip of the dilator and three holes at circumferential sides of the dilator. Moreover, the assembly comprises of a sheath with single lumen to accommodate the dilator to which it fits snugly. The tip of the dilator along with all the holes of entry are located beyond the distal end of the sheath.

Referring to FIG. 3, in one embodiment of the present invention, the single lumen sheath-dilator assembly comprises a dilator with four holes at its distal end such that one hole is at the tip and other three holes at circumferential sides of the dilator. All the four holes enter one common lumen of the dilator which runs all along its length. One of the proximal three holes is marked to define its position with respect to a clock and can be predefined as 12'o clock position. Accordingly, the other two ports will be at 4 and 8 o'clock position respectively. Further, a sheath is coupled to the dilator such that four guide wires enter the dilator-sheath assembly through the four holes, run through the single lumen of the dilator and exit from the proximal single hole of the dilator-sheath assembly (FIG. 4). Although 4 holes and guide wires are shown in this drawing, the number of holes and guide wires used can be variable (more than 1) depending on the internal diameter of the dilator and the choice of the operator In order to track the delivery system over a complex course, the multiple guidewires are first placed inside a patient with the help of catheters and then the sheath-dilator assembly of the present invention is loaded over the guidewires simultaneously and tracked to a desired site. In this manner, the multiple guide wires are utilized to support the introduction of dilator sheath assembly into the patient while tracking the complex course.

The sheath-dilator assembly of the present invention can be used to track complex paths with sharp bends in any part of the human body such as but not limited to main pulmonary artery and its branches, other blood vessels, or organs such as heart and its chambers and liver. Additionally, such assembly allows getting much larger sheaths into main pulmonary artery or its branches to deliver stents mounted on the balloons or even percutaneous pulmonary valve (PPV). These large delivery sheaths can be used even for delivering other valves like mitral, tricuspid and aortic.

Further, as force is distributed in different directions due to different directions of the guide wires, the present invention has the ability to overcome the memory of the sheath-dilator assembly which results in the system getting stuck at any one point of the desired pathway and is seen with the currently available single guide wire sheath-dilator system.

In another embodiment, a delivery system of a percutaneous pulmonary valve as shown in FIG. 6, can be modified by creating more than one side hole on distal end of the delivery system of the valve to track over multiple guidewires.

Yet another embodiment of present invention discloses that internal diameter (ID) of the dilator. The ID can vary from 0.10 to 0.30 inches.

According to another embodiment of present invention the sheath can be selected from 12 Fr sheath, 14 Fr sheath, 16 Fr sheath, 18 Fr sheath, 20 Fr sheath, 22 Fr sheath, 24 Fr sheath, 26 Fr sheath and like. Also the dilator provided could be straight or curved based on the requirements.

Yet again the delivery device comprising multiple entry dilator, wherein the number of guide wire entry is more than one, preferably two to six, most preferably two to three. The guide wires are basically having diameter of 0.035".

In one of the embodiment of present invention discloses a sheath-dilator assembly for tracking inside the heart, or vascular system comprising a dilator with a single lumen at the proximal end and all along its length having multiple holes on distal end to accommodate more than one guide wires. One of the holes is located at the tip of the dilator while the others are located proximally to the distal tip of the dilator but distal to the distal tip of the sheath. The assembly further discloses the number of guide wires and corresponding holes to be more than one, preferably two to six, most preferably two to three.

In another embodiment of present invention discloses a sheath-dilator assembly for tracking inside the heart, or vascular system comprising a dilator with a single lumen at the proximal end and all along its length having multiple holes on distal end to accommodate more than one guide wires. The assembly may comprise one of the holes to be located at the tip of the dilator while the others are located proximally to the distal tip of the dilator but distal to the distal tip of the sheath the number of guide wires and corresponding holes may preferably be more than one, more preferably two to six, most preferably two to three. The assembly may further comprise sheath which is coupled to the dilator in such a way that guide wires enter the dilator-sheath assembly through the holes allocated for each guide wires, run through the single lumen of the dilator and exit from the proximal single hole of the sheath-dilator assembly.

Yet another embodiment of present invention relates to a sheath-dilator assembly for tracking inside the heart, or vascular system comprising a dilator with a single lumen at the proximal end and all along its length having multiple holes on distal end to accommodate more than one guide wires. The assembly further comprises dilator which is adapted to be straight or curved.

Yet another embodiment of present invention relates to a sheath-dilator assembly for tracking inside the heart, or vascular system comprising a dilator with a single lumen at the proximal end and all along its length having multiple holes on distal end to accommodate more than one guide wires. The assembly may comprise one of the holes to be located at the tip of the dilator while the others are located proximally to the distal tip of the dilator but distal to the distal tip of the sheath. The assembly further discloses the number of guide wires and corresponding holes to be more than one, preferably two to six, most preferably two to three. The assembly further comprises dilator which is adapted to be straight or curved. The sheath is further selected from 12 Fr sheath, 14 Fr sheath, 16 Fr sheath, 18 Fr sheath, 20 Fr sheath, 22 Fr sheath, 24 Fr sheath and 26 Fr sheath.

Yet another embodiment of present invention discloses a sheath-dilator assembly for tracking inside the heart, or vascular system comprising a dilator with a single lumen at the proximal end and all along its length having multiple holes on distal end to accommodate more than one guide wires. The number of guide wires and corresponding holes may be more than one, preferably two to six, most preferably two to three. The assembly further comprises dilator which is adapted to be straight or curved. Further, the dilator may have Internal Diameter (ID) of 0.10 to 0.30 inches. The assembly may also comprise the sheath which is selected from 12 Fr sheath, 14 Fr sheath, 16 Fr sheath, 18 Fr sheath, 20 Fr sheath, 22 Fr sheath, 24 Fr sheath and 26 Fr sheath.

In all embodiments of the present invention, a single lumen, multiple entry sheath-dilator assembly is provided for delivering medical devices in different parts of cardiovascular system. The multiple holes allow multiple guidewires to enter the dilator-delivery sheath system distally and exit from a single lumen proximally thereby providing extra support to the delivery system while tracking over complex paths. Such a multi guide wire system has a definite advantage even over a two-wire system because, although two wire system may offer better support as compared to single wire, it will not be as good as a three or four wire system. Also, in two wire system the wires are fixed in their position and therefore overcoming the memory of sheath-dilator system will not be as good as with multi-wire system because of the ability to use the multiple entry holes in various permutations and combinations.

One of the embodiment of present invention discloses a 12 Fr sheath with a straight dilator having a 0.30-inch internal diameter having three guide wire entries (0.035") at the distal end and one common exit proximally.

Yet another embodiment of present invention discloses a 12 Fr sheath with a straight dilator having a 0.20-inch internal diameter having three guide wire entries (0.035") at the distal end and one common exit proximally.

One of the embodiment of present invention discloses a 14 Fr sheath with a straight dilator having a 0.30-inch internal diameter having three guide wire entries (0.035") at the distal end and one common exit proximally.

Yet another embodiment of present invention discloses a 14 Fr sheath with a straight dilator having a 0.20-inch internal diameter having three guide wire entries (0.035") at the distal end and one common exit proximally.

Yet another embodiment of present invention discloses a 16 Fr sheath with a straight dilator having a 0.30-inch internal diameter having three guide wire entries (0.035") at the distal end and one common exit proximally.

Still another embodiment of present invention discloses a 16 Fr sheath with a straight dilator having a 0.20-inch internal diameter having three guide wire entries (0.035") at the distal end and one common exit proximally.

Yet another embodiment of present invention discloses a 12 Fr sheath with a curved dilator having a 0.30-inch internal diameter having three guide wire entries (0.035") at the distal end and one common exit proximally.

Yet another embodiment of present invention discloses a 12 Fr sheath with a curved dilator having a 0.20-inch internal diameter having three guide wire entries (0.035") at the distal end and one common exit proximally.

Yet another embodiment of present invention discloses a 14 Fr sheath with a curved dilator having a 0.30-inch internal diameter having three guide wire entries (0.035") at the distal end and one common exit proximally.

Yet another embodiment of present invention discloses a 14 Fr sheath with a curved dilator having a 0.20-inch internal diameter having three guide wire entries (0.035") at the distal end and one common exit proximally.

One of the embodiment of present invention also discloses a 16 Fr sheath with a curved dilator having a 0.30-inch internal diameter having three guide wire entries (0.035") at the distal end and one common exit proximally.

Another embodiment of present invention also relates to a 16 Fr sheath with a curved dilator having a 0.20-inch internal diameter having three guide wire entries (0.035") at the distal end and one common exit proximally.

Yet another embodiment of present invention discloses a 12 Fr sheath with a straight dilator having a 0.30-inch internal diameter having two guide wire entries (0.035") at the distal end and one common exit proximally.

Yet another embodiment of present invention discloses a 12 Fr sheath with a straight dilator having a 0.20-inch internal diameter having two guide wire entries (0.035") at the distal end and one common exit proximally.

Yet another embodiment of present invention discloses a 14 Fr sheath with a straight dilator having a 0.30-inch internal diameter having two guide wire entries (0.035") at the distal end and one common exit proximally.

Yet another embodiment of present invention also relates to a 14 Fr sheath with a straight dilator having a 0.20-inch internal diameter having two guide wire entries (0.035") at the distal end and one common exit proximally.

Yet another embodiment of present invention discloses a 16 Fr sheath with a straight dilator having a 0.30-inch internal diameter having two guide wire entries (0.035") at the distal end and one common exit proximally.

Still another embodiment of present invention discloses a 16 Fr sheath with a straight dilator having a 0.20-inch internal diameter having two guide wire entries (0.035") at the distal end and one common exit proximally.

Still another embodiment of present invention discloses a 12 Fr sheath with a curved dilator having a 0.30-inch internal diameter having two guide wire entries (0.035") at the distal end and one common exit proximally.

Yet another embodiment of present invention discloses a 12 Fr sheath with a curved dilator having a 0.20-inch internal diameter having two guide wire entries (0.035") at the distal end and one common exit proximally.

Still another embodiment of present invention discloses a 14 Fr sheath with a curved dilator having a 0.30-inch internal diameter having two guide wire entries (0.035") at the distal end and one common exit proximally.

Yet another embodiment of present invention discloses a 14 Fr sheath with a curved dilator having a 0.20-inch internal diameter having two guide wire entries (0.035") at the distal end and one common exit proximally.

Still another embodiment of present invention discloses a 16 Fr sheath with a curved dilator having a 0.30-inch internal diameter having two guide wire entries (0.035") at the distal end and one common exit proximally.

Still another embodiment of present invention discloses a 16 Fr sheath with a curved dilator having a 0.20-inch internal diameter having two guide wire entries (0.035") at the distal end and one common exit proximally.

Still another embodiment of present invention discloses a 18 Fr sheath with a straight dilator having a 0.30-inch internal diameter having three guide wire entries (0.035") at the distal end and one common exit proximally.

Yet another embodiment of present invention discloses a 18 Fr sheath with a straight dilator having a 0.20-inch internal diameter having three guide wire entries (0.035") at the distal end and one common exit proximally.

Still another embodiment of present invention discloses a 20 Fr sheath with a straight dilator having a 0.30-inch internal diameter having three guide wire entries (0.035") at the distal end and one common exit proximally.

Yet another embodiment of present invention discloses a 20 Fr sheath with a straight dilator having a 0.20-inch internal diameter having three guide wire entries (0.035") at the distal end and one common exit proximally.

Still another embodiment of present invention discloses a 22 Fr sheath with a straight dilator having a 0.30-inch internal diameter having three guide wire entries (0.035") at the distal end and one common exit proximally.

Yet another embodiment of present invention discloses a 22 Fr sheath with a straight dilator having a 0.20-inch internal diameter having three guide wire entries (0.035") at the distal end and one common exit proximally.

Still another embodiment of present invention discloses a 24 Fr sheath with a straight dilator having a 0.30-inch internal diameter having three guide wire entries (0.035") at the distal end and one common exit proximally.

Yet another embodiment of present invention discloses a 24 Fr sheath with a straight dilator having a 0.20-inch internal diameter having three guide wire entries (0.035") at the distal end and one common exit proximally.

Still another embodiment of present invention discloses a 26 Fr sheath with a straight dilator having a 0.30-inch internal diameter having three guide wire entries (0.035") at the distal end and one common exit proximally.

Still another embodiment of present invention discloses a 26 Fr sheath with a straight dilator having a 0.20-inch internal diameter having three guide wire entries (0.035") at the distal end and one common exit proximally.

Yet another embodiment of present invention discloses a 18 Fr sheath with a curved dilator having a 0.30-inch internal diameter having three guide wire entries (0.035") at the distal end and one common exit proximally.

Yet another embodiment of present invention discloses a 18 Fr sheath with a curved dilator having a 0.20-inch internal diameter having three guide wire entries (0.035") at the distal end and one common exit proximally.

Yet another embodiment of present invention discloses a 20 Fr sheath with a curved dilator having a 0.30-inch internal diameter having three guide wire entries (0.035") at the distal end and one common exit proximally.

Yet another embodiment of present invention discloses a 20 Fr sheath with a curved dilator having a 0.20-inch internal diameter having three guide wire entries (0.035") at the distal end and one common exit proximally.

Yet another embodiment of present invention discloses a 22 Fr sheath with a curved dilator having a 0.30-inch internal diameter having three guide wire entries (0.035") at the distal end and one common exit proximally.

Yet another embodiment of present invention discloses a 22 Fr sheath with a curved dilator having a 0.20-inch internal diameter having three guide wire entries (0.035") at the distal end and one common exit proximally.

Yet another embodiment of present invention discloses a 24 Fr sheath with a curved dilator having a 0.30-inch internal diameter having three guide wire entries (0.035") at the distal end and one common exit proximally.

Yet another embodiment of present invention discloses a 24 Fr sheath with a curved dilator having a 0.20-inch internal diameter having three guide wire entries (0.035") at the distal end and one common exit proximally.

Still another embodiment of present invention discloses a 26 Fr sheath with a curved dilator having a 0.30-inch internal diameter having three guide wire entries (0.035") at the distal end and one common exit proximally.

Yet another embodiment of present invention discloses a 26 Fr sheath with a curved dilator having a 0.20-inch internal diameter having three guide wire entries (0.035") at the distal end and one common exit proximally.

Yet another embodiment of present invention discloses a 18 Fr sheath with a straight dilator having a 0.30-inch internal diameter having two guide wire entries (0.035") at the distal end and one common exit proximally.

Still another embodiment of present invention discloses a 18 Fr sheath with a straight dilator having a 0.20-inch internal diameter having two guide wire entries (0.035") at the distal end and one common exit proximally.

Yet another embodiment of present invention discloses a 20 Fr sheath with a straight dilator having a 0.30-inch internal diameter having two guide wire entries (0.035") at the distal end and one common exit proximally.

Still another embodiment of present invention discloses a 20 Fr sheath with a straight dilator having a 0.20-inch internal diameter having two guide wire entries (0.035") at the distal end and one common exit proximally.

Yet another embodiment of present invention discloses a 22 Fr sheath with a straight dilator having a 0.30-inch internal diameter having two guide wire entries (0.035") at the distal end and one common exit proximally.

Still another embodiment of present invention discloses a 22 Fr sheath with a straight dilator having a 0.20-inch internal diameter having two guide wire entries (0.035") at the distal end and one common exit proximally.

Yet another embodiment of present invention discloses a 24 Fr sheath with a straight dilator having a 0.30-inch internal diameter having two guide wire entries (0.035") at the distal end and one common exit proximally.

Still another embodiment of present invention discloses a 24 Fr sheath with a straight dilator having a 0.20-inch internal diameter having two guide wire entries (0.035") at the distal end and one common exit proximally.

Still another embodiment of present invention discloses a 26 Fr sheath with a straight dilator having a 0.30-inch internal diameter having two guide wire entries (0.035") at the distal end and one common exit proximally.

Yet another embodiment of present invention discloses a 26 Fr sheath with a straight dilator having a 0.20-inch internal diameter having two guide wire entries (0.035") at the distal end and one common exit proximally.

Still another embodiment of present invention discloses a 18 Fr sheath with a curved dilator having a 0.30-inch internal diameter having two guide wire entries (0.035") at the distal end and one common exit proximally.

Still another embodiment of present invention discloses a 18 Fr sheath with a curved dilator having a 0.20-inch internal diameter having two guide wire entries (0.035") at the distal end and one common exit proximally.

Still another embodiment of present invention discloses a 20 Fr sheath with a curved dilator having a 0.30-inch internal diameter having two guide wire entries (0.035") at the distal end and one common exit proximally.

Still another embodiment of present invention discloses a 20 Fr sheath with a curved dilator having a 0.20-inch internal diameter having two guide wire entries (0.035") at the distal end and one common exit proximally.

Still another embodiment of present invention discloses a 22 Fr sheath with a curved dilator having a 0.30-inch internal diameter having two guide wire entries (0.035") at the distal end and one common exit proximally.

Still another embodiment of present invention discloses a 22 Fr sheath with a curved dilator having a 0.20-inch internal diameter having two guide wire entries (0.035") at the distal end and one common exit proximally.

Still another embodiment of present invention discloses a 24 Fr sheath with a curved dilator having a 0.30-inch internal diameter having two guide wire entries (0.035") at the distal end and one common exit proximally.

Still another embodiment of present invention discloses a 24 Fr sheath with a curved dilator having a 0.20-inch internal diameter having two guide wire entries (0.035") at the distal end and one common exit proximally.

One of the embodiments of present invention discloses a 26 Fr sheath with a curved dilator having a 0.30-inch internal diameter having two guide wire entries (0.035") at the distal end and one common exit proximally.

Yet another embodiment of present invention discloses a 26 Fr sheath with a curved dilator having a 0.20-inch internal diameter having two guide wire entries (0.035") at the distal end and one common exit proximally.

In an exemplary embodiment of the present invention, multiple guide wires are placed in an artery, vessel or a heart chamber and then a percutaneous valve is pushed over the multiple guidewires to a desired destination. Therefore, the multiple guide wires offer extra support to the percutaneous valve system to track over to the desired destination in the artery, vessel or the heart.

Another exemplary embodiment of present invention discloses a delivery system with multiple entries and a single exit to deliver vascular grafts (Covered stents) in blood vessels with side branches. These grafts can occlude the side branches unless the grafts are perforated exactly opposite the origin of the branch and delivered over multiple wires placed in these respective branches.

Some of the non-limiting advantages of the present invention are
1. Offer extra support to delivery systems.
2. Tracking complex paths and sharp bends.
3. Overcome memory of the delivery system.

Although a multiple hole, single lumen dilator sheath assembly has been described in language specific to structural features, it is to be understood that the embodiments disclosed in the above section are not necessarily limited to the specific methods or devices described herein. Rather, the specific features are disclosed as examples of implementations of a multiple hole, single lumen dilator sheath assembly.

The invention claimed is:

1. A sheath-dilator assembly comprising a dilator with a single lumen at the proximal end and all along its length, the dilator having multiple holes on its distal end to accommodate more than one multiple guide wires simultaneously to help track over a complex path of the human body and reach a desired destination(•); wherein diameter of each of the holes is 0.035"; wherein internal diameter (ID) of the dilator is from 0.10 to 0.30 inches.

2. The sheath-dilator assembly as claimed in claim 1, wherein one hole of said multiple holes is located at the tip of the dilator while holes other than the said one hole of the said multiple holes are located proximally to the distal tip of the dilator but distal to the distal tip of a sheath.

3. The sheath-dilator assembly as claimed in claim 1, wherein a sheath is coupled to the dilator such that more than one guide wires enter the dilator-sheath assembly through a corresponding hole allocated for each guide wire, run through the single lumen of the dilator and exit from the proximal single hole of the dilator-sheath assembly.

4. The sheath-dilator assembly as claimed in claim 3, wherein the number of guide wires and corresponding holes is more than one, preferably two to six, most preferably two to three.

5. The sheath-dilator assembly as claimed in claim 1, wherein a sheath is selected from 12 Fr sheath, 14 Fr sheath, 16 Fr sheath, 18 Fr sheath, 20 Fr sheath, 22 Fr sheath, 24 Fr sheath and 26 Fr sheath.

6. The sheath-dilator assembly as claimed in claim 1, wherein the dilator is straight or curved.

7. A sheath-dilator assembly for tracking inside the heart, or vascular system comprising a dilator with a single lumen at the proximal end and all along its length, the dilator having multiple corresponding holes on a distal end to accommodate multiple guide wires simultaneously;
  wherein one hole is located at a tip of the dilator while the others are located proximally to the distal tip of the dilator but distal to a distal tip of a sheath;
  wherein the number of guide wires and corresponding holes is more than one, preferably two to six, most preferably two to three; and
  wherein the diameter of the holes is at least 0.035" and wherein an internal diameter (ID) of the dilator is from 0.10 to 0.30 inches.

8. A sheath-dilator assembly for tracking inside the heart or any one of its chambers, or vascular system comprising a dilator with a single lumen at a proximal end and all along its length, the dilator having multiple corresponding holes on a distal end to accommodate multiple guide wires simultaneously;
  wherein one hole is located at a tip of the dilator while the others are located proximal to the distal tip of the dilator but distal to a distal tip of a sheath; and
  wherein the number of corresponding holes is more than one, preferably two to six, most preferably two to three;
  wherein the sheath is coupled to the dilator such that the multiple guide wires enter the dilator-sheath assembly simultaneously through the holes allocated for each guide wire, run through the single lumen of the dilator and exit from the proximal single hole of the dilator-sheath assembly; and
  wherein the diameter of the holes is at least 0.035" and wherein an internal diameter (ID) of the dilator is from 0.10 to 0.30 inches.

* * * * *

UNITED STATES PATENT AND TRADEMARK OFFICE
CERTIFICATE OF CORRECTION

PATENT NO. : 12,011,559 B2
APPLICATION NO. : 16/972653
DATED : June 18, 2024
INVENTOR(S) : Bharat V. Dalvi et al.

Page 1 of 1

It is certified that error appears in the above-identified patent and that said Letters Patent is hereby corrected as shown below:

In the Claims

Column 11, Line 26, delete "desired destination(·);" and insert --desired destination;--

Signed and Sealed this
Seventh Day of January, 2025

Derrick Brent
*Acting Director of the United States Patent and Trademark Office*